(12) United States Patent
Maissami

(10) Patent No.: US 6,913,464 B2
(45) Date of Patent: Jul. 5, 2005

(54) COMPOSITION APPLICATOR TIP

(75) Inventor: Fari Maissami, Hinsdale, IL (US)

(73) Assignee: Denbur, Inc., Westmont, IL (US)

( * ) Notice: Subject to any disclaimer, the term of this patent is extended or adjusted under 35 U.S.C. 154(b) by 48 days.

(21) Appl. No.: 10/347,894

(22) Filed: Jan. 20, 2003

(65) Prior Publication Data
US 2004/0142301 A1 Jul. 22, 2004

(51) Int. Cl.⁷ .............................................. A46B 11/02
(52) U.S. Cl. ............................ 433/89; 222/386; 433/87
(58) Field of Search .............................. 433/89, 90, 87; 222/386

(56) References Cited

U.S. PATENT DOCUMENTS

| | | |
|---|---|---|
| 767,469 A | 8/1904 | Ziegler et al. |
| 2,145,570 A | 1/1939 | Miettunen |
| 2,293,211 A | 8/1942 | Mureau |
| 3,048,170 A | 8/1962 | Lemos |
| RE25,483 E | 11/1963 | Lemos |
| 3,359,992 A | 12/1967 | Cishek et al. |
| 3,417,762 A | 12/1968 | Hall |
| 3,499,686 A | 3/1970 | Landen et al. |
| 4,199,270 A | 4/1980 | Tomasini |
| 4,672,953 A | 6/1987 | DiVito |
| 4,738,669 A | 4/1988 | Vlock |
| 4,808,022 A | 2/1989 | Iizuka et al. |
| 4,963,046 A | 10/1990 | Eguchi |
| 4,997,371 A | 3/1991 | Fischer |
| 5,154,523 A | 10/1992 | Devreeze |
| 5,244,388 A | 9/1993 | Frush |
| 5,246,371 A | 9/1993 | Fischer |
| 5,269,684 A | 12/1993 | Fischer |
| 5,286,257 A | 2/1994 | Fischer |
| 5,816,804 A | 10/1998 | Fischer |
| 6,059,570 A | 5/2000 | Dragan et al. |
| D441,074 S | 4/2001 | Mark |
| D444,229 S | 6/2001 | Mark |
| D447,242 S | 8/2001 | Mark |
| 6,376,025 B1 | 4/2002 | Mark |
| 2003/0079305 A1 * | 5/2003 | Takahata et al. .............. 15/22.1 |

FOREIGN PATENT DOCUMENTS

| | | |
|---|---|---|
| EP | 0 582 361 A1 | 2/1994 |
| FR | 2 288 495 | 5/1976 |
| GB | 2 203 636 A | 10/1988 |
| WO | WO 89/12428 | 12/1989 |
| WO | WO 94/09681 | 5/1994 |

OTHER PUBLICATIONS

Microbrush® Products, 2 pages.
Microbrush® Products, *Microbrush™ Disposable Applicators*, 2 pages.
Microbrush® Products, *Blockbuster New Products Special*, Flowthru® Microbrush®Style or Smartbrush®Classic.
Ultradent Products Inc., *Here's a couple of tips for sealant procedures in half the time.*
Ultradent Products Inc., *Ultraseal XT® plus™*.

* cited by examiner

Primary Examiner—Cary E. O'Connor
Assistant Examiner—Candice C. Stokes
(74) Attorney, Agent, or Firm—Pauley Petersen & Erickson

(57) ABSTRACT

An applicator tip for applying a composition to a tooth surface includes a structural body having a closed distal end portion and an inlet formed opposite the closed distal end portion. Preferably, but not necessarily, a plurality of fibers coat at least a portion of the closed distal end portion of the applicator tip. The applicator tip includes an axial opening formed within the structural body proximal to the closed distal end portion such that the structural body forms a channel that provides fluidic communication between the inlet and the axial opening.

18 Claims, 4 Drawing Sheets

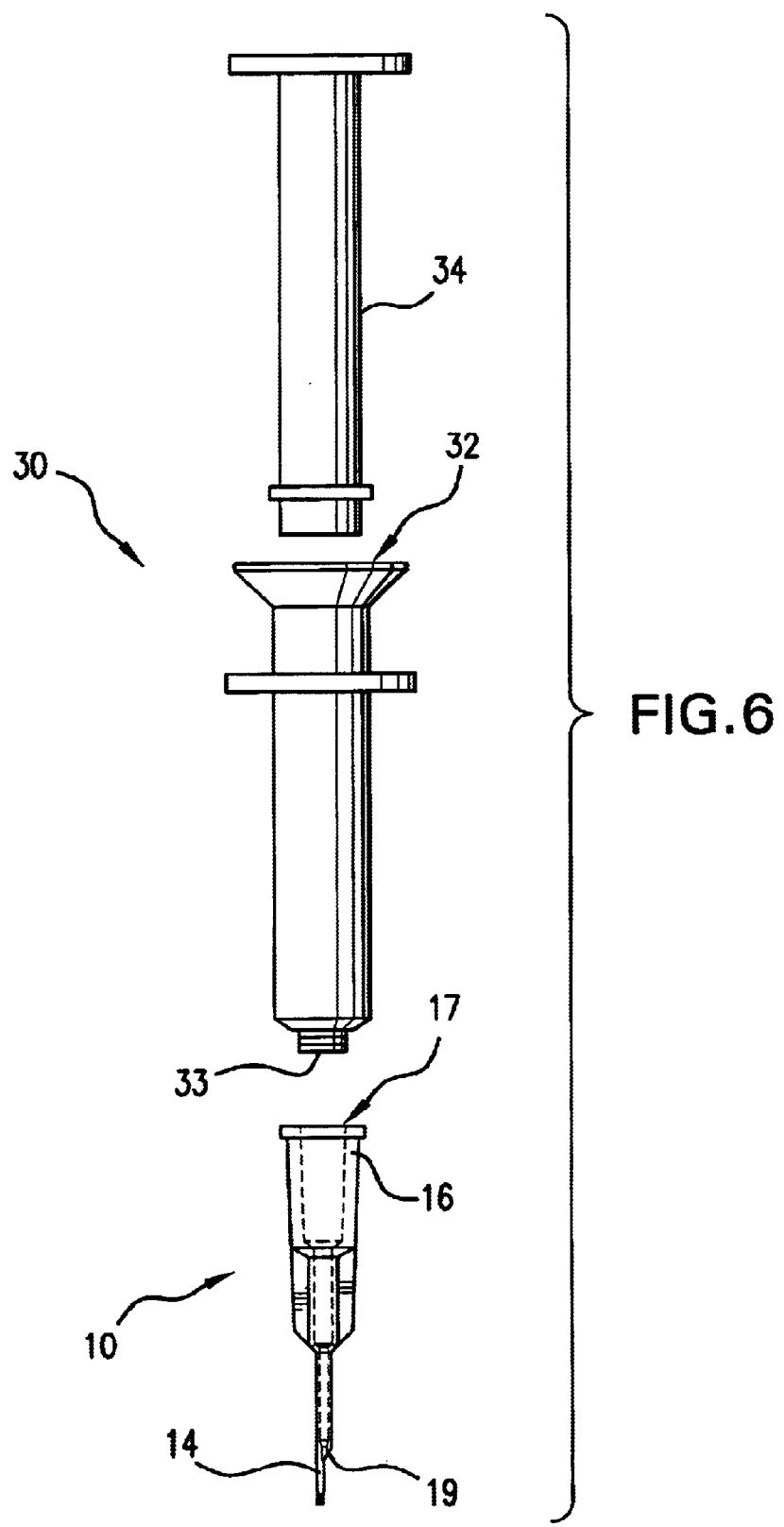

COMPOSITION APPLICATOR TIP

BACKGROUND OF THE INVENTION

This invention relates generally to a device and method for applying a dental composition to a tooth surface and, more particularly, to an applicator tip for a hand-operated application device having a closed distal end portion preferably, but not necessarily, coated or flocked with a plurality of fibers and an axial opening formed proximal to the closed distal end portion for applying a dental composition to the tooth surface.

Delivery tips or applicators are generally used throughout dentistry to apply a dental composition to a tooth surface or region. Typically, the delivery tips are used in combination with a delivery device, such as a syringe to deliver the dental compositions to the tooth surface. The dental compositions may include hemostatic agents, etchants, bonding agents, disinfectants, sealants and impression materials, for example.

Many such delivery tips are connected to the syringe and form an opening at a distal end of the delivery tip to provide fluidic communication between the opening and the syringe chamber. The dental composition contained within the syringe chamber is urged through the opening at the distal end of the delivery tip using a plunger that is insertable into the syringe chamber. Typically, a plurality of fibrous bristles are disposed about a periphery of the opening. Such bristles can be used to agitate or spread the deposited dental composition onto a desired area of the tooth surface.

Several problems or shortcomings result from the delivery tip having a plurality of bristles disposed about the periphery of the opening formed at the distal end of the tip. For example, the bristles disposed about the periphery of the opening at the distal end of the delivery tip may hinder or obstruct the dentist's view of the dental composition as it dispensed from the delivery tip onto the tooth surface. A clear, unobstructed view is important for the dentist to monitor and control the precise flow of the dental composition onto the tooth surface, particularly when the dental composition includes a highly viscous impression material or an adhesive material, for example. The ability of the dentist to precisely control the spreading or disbursing of the dental composition onto or within a desired area or region of the tooth surface is compromised by the inability to monitor and control the amount of dental composition deposited onto the tooth surface. Further, the bristles disposed about the periphery of the opening may interfere with the dental composition as it is dispensed from the delivery tip, thereby interfering with the flow of the dental composition and/or obstructing the opening.

In view of the above, there is a need and a demand for an improved applicator tip for use in combination with an application device. In particular, there is a need and a demand for an applicator tip that provides for precise and controllable application of dental compositions onto a tooth surface, without interfering with the flow of the dental composition through the applicator tip and without obstructing the dentist's view of the delivery tip opening and the tooth surface.

SUMMARY OF THE INVENTION

A general object of the invention is to provide an improved applicator tip.

A more specific objective of the invention is to overcome one or more of the problems described above.

The general object of the invention can be attained, at least in part, through an applicator tip having a structural body with a closed distal end portion and a base end portion forming an inlet opposite the closed distal end portion. An axial opening is formed within a sidewall of the structural body proximal to the closed distal end portion. The structural body further forms a channel to provide fluidic communication between the inlet and the axial opening. In one preferred embodiment of this invention, at least a portion of the closed distal end portion is flocked or coated with a plurality of fibers.

The prior art generally fails to provide an applicator tip having a closed distal end portion coated or covered with a plurality of fibers. Additionally, the prior art generally fails to provide an applicator tip that forms an axial opening within the sidewall of the structural body proximal to the distal end portion of the applicator tip, so that the dentist can monitor and control the flow of a dental composition through the applicator tip axial opening onto the tooth surface.

The invention further comprehends a combination of the applicator tip with an application apparatus or device that forms a chamber having a discharge opening in fluidic communication with the applicator tip inlet. For example, the invention comprehends a composition application device including a syringe that forms a chamber having a discharge opening. The chamber contains a dental composition for depositing on a tooth surface. A plunger is positionable within the chamber to urge the dental composition through the discharge opening and into an inlet formed in an applicator tip. The applicator tip includes a structural body that forms an axial opening proximal to a closed distal end portion and a channel along a longitudinal axis of the structural body to provide fluidic communication between the inlet and the axial opening.

Other objects and advantages will be apparent to those skilled in the art from the following detailed description taken in conjunction with the appended claims and drawings.

BRIEF DESCRIPTION OF THE DRAWINGS

FIG. 6 is a schematic drawing of the applicator tip shown in FIG. 1 removably attached to an application device according to one preferred embodiment of the invention.

DETAILED DESCRIPTION OF THE INVENTION

The present invention provides an applicator tip for precisely applying or depositing a desired amount of a dental composition onto or within a tooth surface location or region. Suitable dental compositions include, but are not limited to, hemostatic agents, etchants, bonding agents, disinfectants, antimicrobial agents, sealants, flowable composites, dental impression materials, and the like. In one preferred embodiment of the invention, the applicator tip is used in combination with an application device or apparatus, such as a syringe, for controllably applying the dental composition onto the tooth surface location.

Figure 1:
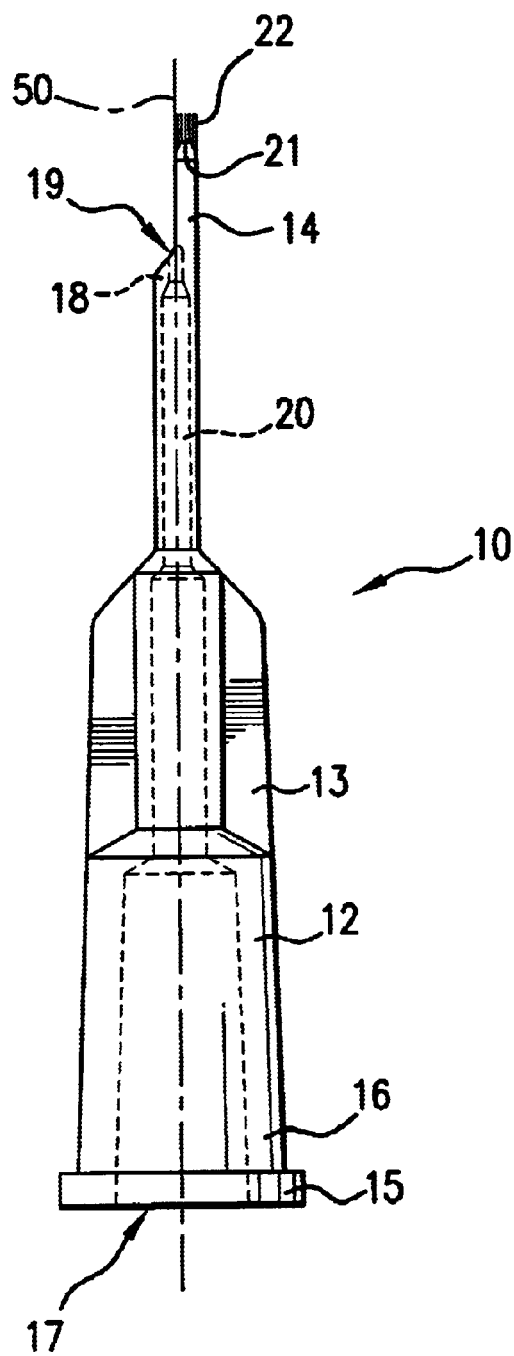
FIG. 1 is a schematic drawing of an applicator tip according to one preferred embodiment of the invention.
Figure 2:
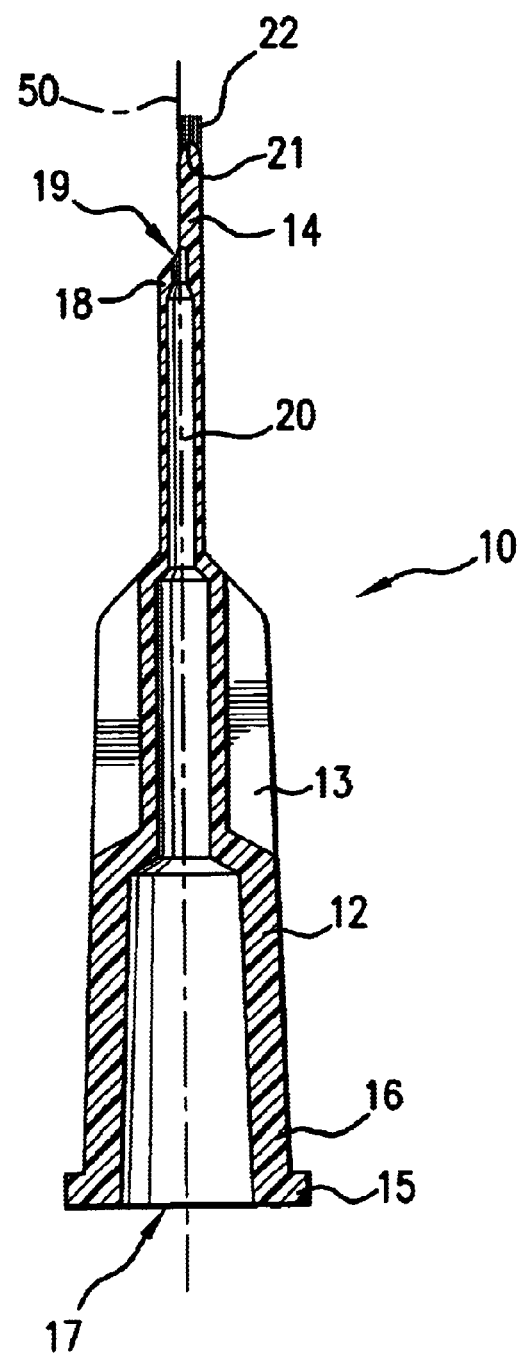
FIG. 2 is a cross-sectional, schematic drawing of the applicator tip shown in FIG. 1 according to one preferred embodiment of the invention.
Figure 3:
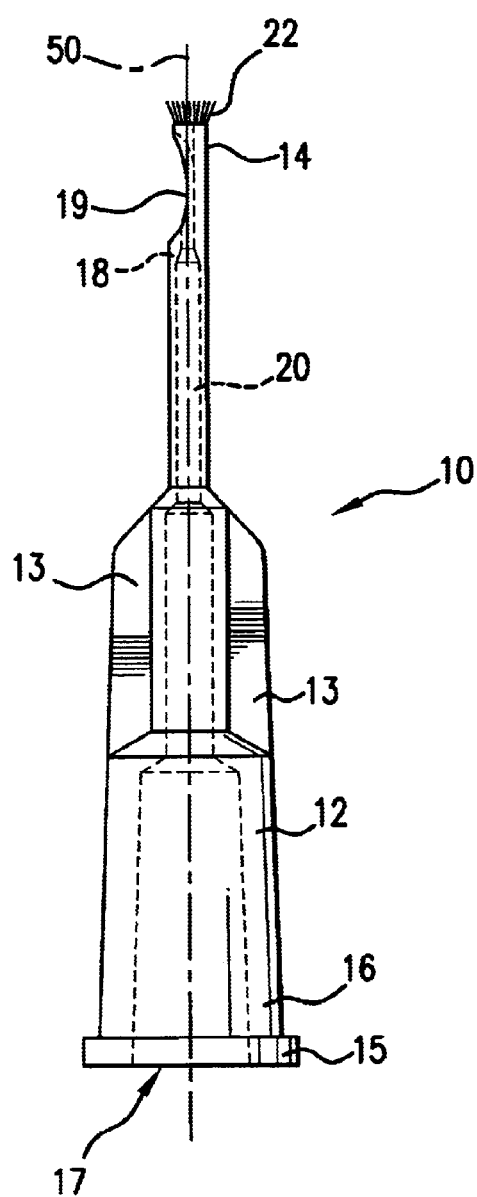
FIG. 3 is a schematic drawing of an applicator tip according to one preferred embodiment of the invention.
Figure 4:
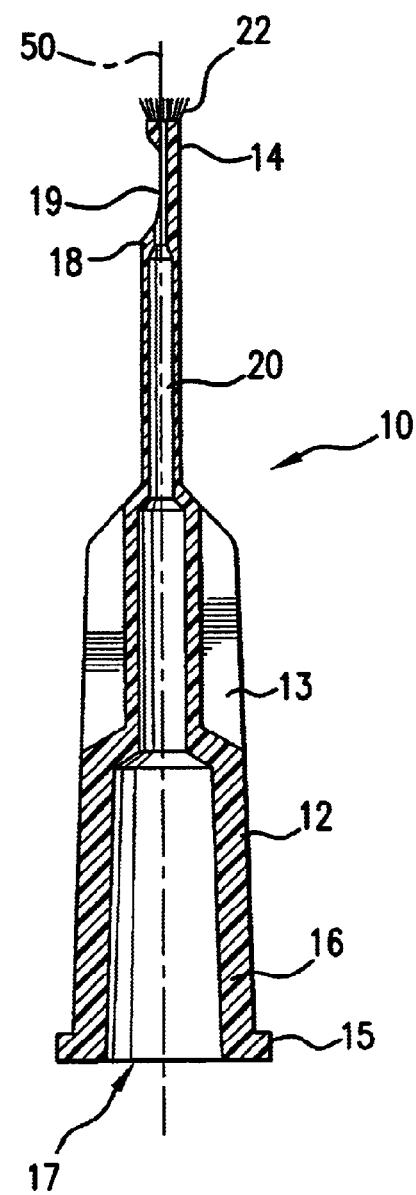
FIG. 4 is a cross-sectional, schematic drawing of the applicator tip shown in FIG. 3 according to one preferred embodiment of the invention.
Figure 5:
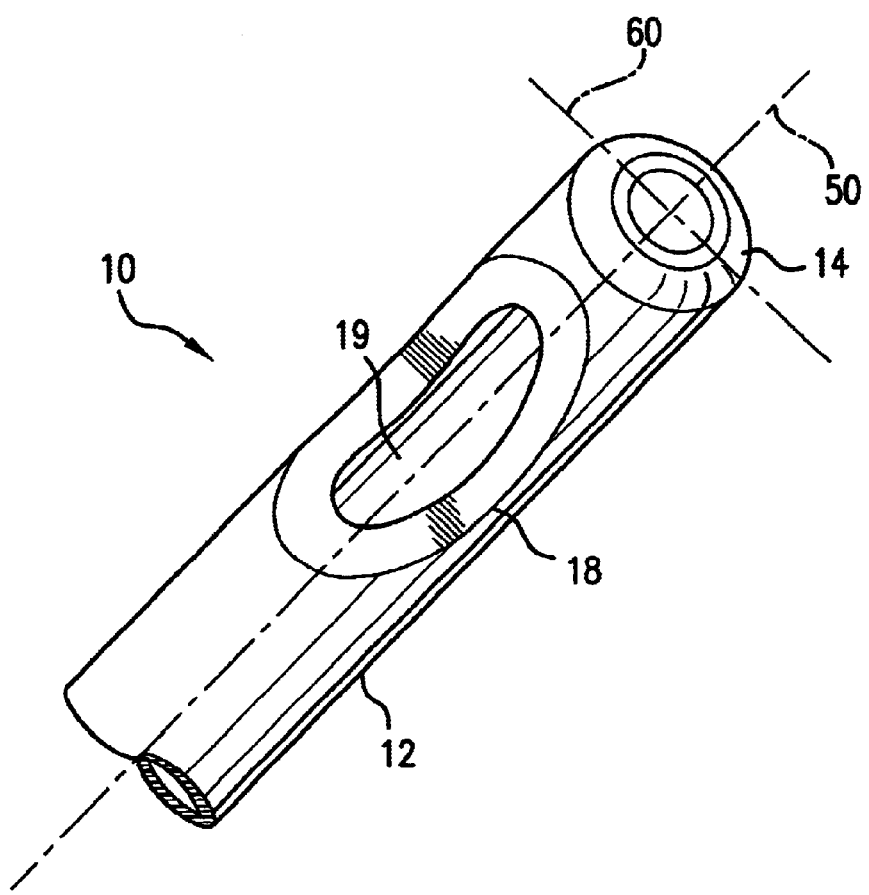
FIG. 5 is a schematic drawing of a portion of an applicator tip, illustrating an axial opening formed in a sidewall of the structural body proximal to a closed distal end portion of the applicator tip according to one preferred embodiment of the invention.

Referring to FIGS. 1–4, applicator tip 10 for applying the dental composition onto the tooth surface includes a structural body 12 having a closed distal end portion 14 and a base end portion 16 forming an inlet 17 opposite closed distal end portion 14. Preferably, but not necessarily, closed distal end portion 14 has a generally curved or arcuate tip surface 21, as shown in FIGS. 1 and 2. The term "closed" as used throughout this specification in connection with distal end portion 14 refers to a portion of applicator tip 10 that is solid or does not form any portion of a channel 20 formed along a longitudinal axis 50 of applicator tip 10. As shown for example in FIGS. 1–4, closed distal end portion 14 extends distally beyond axial opening 19 a desired length to allow the dentist to distribute the deposited dental composition onto or within a desired tooth surface area or region, as discussed in greater detail below. Preferably, closed distal end portion 14 is tapered along longitudinal axis 50 to tip surface 21, as shown in FIGS. 1 and 2. The tapering of closed distal end portion 14 as well as the curvature of curved tip surface 21 assists the dentist in distributing the dental composition to the desired tooth surface area or region.

Preferably, but not necessarily, at least a portion of structural body 12 is made of a bendable material, such as a bendable plastic or metal material. Other suitable bendable materials known to those having ordinary skill in the art may be used to form structural body 12. Alternatively, structural body 12 may be made of a rigid material, such as a rigid plastic, metal or composite material. In one embodiment of the invention, applicator tip 10 may include a combination of rigid and bendable materials. For example, base end portion 16 may be made of rigid plastic material and distal end portion 14 may be made of an arcuate-shaped metal material.

As shown in FIGS. 1–4, applicator tip 10 may include at least one and preferably a plurality of tabs 13 to assist in attaching or connecting applicator tip 10 to the application device or apparatus. Additionally, applicator tip 10 may include a peripheral lip or ledge 15 that extends radially outwardly from applicator tip base end portion 16 and provides a sealed connection surface with the applicator device or apparatus to prevent undesired leakage of the dental composition at the applicator tip/application device connection. Preferably, applicator tip 10 is made of a material that is compatible with respect to the dental compositions deposited onto the tooth surface or region using applicator tip 10.

Referring to FIGS. 1–5, at least a portion of the structural body 12 forms a cylindrical sidewall 18. An axial opening 19 is formed in sidewall 18 proximal to closed distal end portion 14. The term "axial" refers to a position or location of axial opening 19 relative to a longitudinal axis 50 of structural body 12. As shown for example in FIG. 5, axial opening 19 extends along sidewall 18 generally parallel to the longitudinal axis 50 and generally perpendicular to a radial axis 60 of structural body 12, as opposed to extending in a generally radial or cross-sectional direction along radial axis 60. Axial opening 19 may have any suitable shape. For example, axial opening 19 may have a circular, elliptical, polygonal or tapered shape.

As shown in FIG. 1 for example, structural body 12 forms a channel 20 that extends generally along longitudinal axis 50 from base end portion 16 to axial opening 19 to provide fluidic communication between inlet 17 and axial opening 19. Preferably, channel 20 has a circular cross-sectional area. It is apparent to those skilled in the art that channel 20 may have any suitable cross-sectional shape, such as elliptical or triangular, for example.

In one preferred embodiment of the invention, a plurality of fibers 22 are disposed relative to distal end portion 14. For example, the fibers 22 may be disposed or attached at distal end portion 14 to cover at least a portion of distal end portion 14. Preferably, fibers 22 are adhered or attached to distal end portion 14 using a flocking procedure, wherein fibers are sprayed onto an outer surface of structural body 12 at distal end portion 14 so that fibers 22 adhere electrostatically to the outer surface of structural body 12. Other suitable attachment means, such as adhesive attachment processes, may be used to attach or adhere fibers 22 to structural body 12. Preferably, fibers 22 are made of a non-lint nylon that does not absorb the dental composition as the dental composition is delivered and applied to the tooth surface. Thus, as pressure is applied to the tooth surface using applicator tip 10, the dental composition is easily transferred from fibers 22 to the tooth surface. Other suitable materials apparent to those having ordinary skill in the art may be used to form fibers 22.

In one preferred embodiment of this invention, fibers 22 are disposed on the distal end portion 14 but are not disposed relative to axial opening 19. Because fibers 22 are disposed distal to axial opening 19, the dentist's view of the tooth surface or region and axial opening 19 is not obstructed. Further, fibers 22 do not interfere with the flow of the dental composition from axial opening 19 onto the tooth surface or region. The dental composition applied to or disposed on the tooth surface or region can be agitated by the movement of fibers 22 to remove entrapped air bubbles from the dental composition. Additionally, the fibers 22 may be used to coat and/or spread the dental composition on the tooth surface or region. In an alternative embodiment of this invention, applicator tip 10 may be free or void of fibers 22.

Referring to FIG. 6, applicator tip 10 is operatively attached or connected to an application device or apparatus. For example, applicator tip 10 may be releaseably attachable or connectable to a syringe 30 or other device used by the dentist to deposit the dental compositions onto the tooth surface or region. Preferably, applicator tip 10 is threadedly connectable to syringe 30. Other suitable mechanical connections, such as press-fitting, may be used to removably connect applicator tip 10 to syringe 30. It is apparent to those skilled in the art that applicator tip 10 can be adapted for use with other suitable means for applying or depositing a desired quantity of dental composition onto the tooth surface or region.

Syringe 30 forms a chamber 32 having a discharge opening 33 in fluidic communication with applicator tip inlet 17. A supply of dental composition for applying to the selected tooth surface or region is contained or stored within chamber 32. As shown in FIG. 6, a plunger 34 is positionable and movable within chamber 32 to urge the dental composition through discharge opening 33 and into applicator tip channel 20. For example, inlet end portion 16 may be removably connectable to syringe 30 to form fluidic communication between discharge opening 33 and inlet 17. The dental composition is controllably urged through channel 20 and onto the desired tooth surface or region.

Thus, the invention provides an applicator tip, for use in combination with an application device or apparatus for example, having a closed distal end portion coated or flocked with a plurality of fibers and an axial opening formed in the sidewall of the structural body proximal to the closed distal end portion so that the dentist can closely monitor and precisely control the flow of the dental composition through the deliver tip to the tooth surface or region, without the fibers obstructing the dentist's view of the tooth surface and/or the dental composition flow from the applicator tip, and without the fibers physically interfering with the dental composition flow from the axial opening.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An applicator tip for applying a composition to a tooth surface comprising:
    a structural body having a closed distal end portion and an inlet formed opposite the closed distal end portion;
    a plurality of fibers coating at least a portion of the closed distal end portion: and an axial opening formed within a sidewall of the structural body proximal to the closed distal end portion, the structural body forming a channel providing fluidic communication between the inlet and the axial opening, all of the plurality of fibers being positioned distal to the axial opening, the sidewall having a generally smooth surface to facilitate the application of the composition to the tooth surface.

2. The applicator tip of claim 1 wherein the structural body comprises a rigid material.

3. The applicator tip of claim 1 wherein the structural body comprises a bendable material.

4. The applicator tip of claim 1 wherein the applicator tip is connectable to a syringe.

5. The applicator tip of claim 4 wherein the applicator tip is threadedly connectable to the syringe.

6. The applicator tip of claim 1 wherein the channel extends along at least a portion of a longitudinal axis of the structural body.

7. The applicator tip of claim 6 wherein the axial opening is formed generally parallel to the longitudinal axis.

8. The applicator tip of claim 6 wherein the axial opening is formed generally perpendicular to a radial axis of the structural body.

9. The applicator tip of claim 1 wherein the axial opening is one of circular, elliptical, polygonal or tapered shaped.

10. The applicator tip of claim 1 wherein the closed distal end portion has an arcuate shape.

11. A bendable applicator tip for applying a composition to a tooth surface comprising:
    a structural body having a closed distal end portion and a base end portion forming an inlet, and at least a portion of the structural body forming a cylindrical sidewall having a generally smooth surface;
    a plurality of fibers coating at least a portion of the closed distal end portion;
    an axial opening formed in the sidewall proximal to the closed distal end portion; and
    a channel formed within the structural body providing fluidic communication between the inlet and the axial opening;
    all of the plurality of fibers being positioned distal to the axial opening.

12. The bendable applicator tip of claim 11 wherein the applicator tip is connectable to a syringe.

13. The applicator tip of claim 11 wherein the applicator tip is threadedly connectable to a syringe.

14. A combination comprising:
    the applicator tip of claim 11; and
    an application device forming a chamber having a discharge opening in fluidic communication with the inlet of the applicator tip.

15. A composition application device comprising:
    a syringe forming a chamber having a discharge opening, the chamber containing a composition for applying to a tooth surface;
    a plunger positionable within the chamber urging the composition through the discharge opening; and
    an applicator tip comprising a structural body having a closed distal end portion and an inlet end portion forming an inlet, the inlet end portion removably connectable to the syringe to form fluidic communication between the discharge opening and the inlet;
    a plurality of fibers coating at least a portion of the closed distal end portion;
    an axial opening formed within a sidewall of the structural body proximal to the closed distal end portion, the sidewall having a generally smooth surface free of fibers between the inlet and the axial opening to facilitate application of the composition to the tooth surface; and
    a channel formed within the structural body providing fluidic communication between the inlet and the axial opening.

16. The application device of claim 15 wherein the structural body comprises a rigid material.

17. The application device of claim 15 wherein the structural body comprises a bendable material.

18. The application device of claim 15 wherein the inlet end portion is threadedly connectable to the syringe.

* * * * *